(12) United States Patent
Ito

(10) Patent No.: US 7,796,724 B2
(45) Date of Patent: Sep. 14, 2010

(54) X-RAY FLUOROSCOPIC SYSTEM

(75) Inventor: Seiji Ito, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/517,063

(22) PCT Filed: Nov. 27, 2007

(86) PCT No.: PCT/JP2007/072809

§ 371 (c)(1), (2), (4) Date: May 30, 2009

(87) PCT Pub. No.: WO2008/066017

PCT Pub. Date: Jun. 5, 2008

(65) Prior Publication Data

US 2010/0074404 A1    Mar. 25, 2010

(30) Foreign Application Priority Data

Dec. 1, 2006    (JP) .............................. 2006-326228

(51) Int. Cl.
*H05G 1/30* (2006.01)
(52) U.S. Cl. ........................................ 378/42; 378/208
(58) Field of Classification Search ................... 378/55, 378/208, 189, 190, 42, 62, 205, 207, 196, 378/197

See application file for complete search history.

(56) References Cited

U.S. PATENT DOCUMENTS

| 7,539,284 B2* | 5/2009 | Besson ........................ 378/62 |
| 2004/0096029 A1* | 5/2004 | Shiota et al. .................. 378/42 |
| 2008/0069304 A1* | 3/2008 | Muszak et al. .............. 378/114 |

* cited by examiner

*Primary Examiner*—Hoon Song
(74) *Attorney, Agent, or Firm*—Cheng Law Group, PLLC

(57) ABSTRACT

An X-ray fluoroscopic system which is capable of highly accurately performing tilting tracking or rotational tracking by a simple operation in an observation work without inputting a distance from the surface of a table and an observed point of an object of fluoroscopy and without performing a calibration operation for obtaining the distance in advance. The X-ray fluoroscopic system having a tracking function of obtaining a moving amount of the table, which is necessary for performing tilting or rotational tracking, and moving the table, based on an arithmetic operation using a distance h obtained by totalizing a distance d from the surface of the table to an observed point V, and a distance z from the surface of the table to an X-ray focal point $1a$, a defined value or arbitrary input value is used as an initial value of the distance h, and a shift amount of the observed point V occurred from tracking is used to update the distance h by specifying the observed point V on a screen after tracking, thereby tilt (rotation) tracking accuracy is gradually improved.

2 Claims, 8 Drawing Sheets

X-RAY FLUOROSCOPIC SYSTEM

TECHNICAL FIELD

The present invention relates to an X-ray fluoroscopic system, more particularly to an X-ray fluoroscopic system applicable to a system that displays a fluoroscoped image of an object of fluoroscopy on a monitor screen or captures the image, and an X-ray CT scanner that builds a CT image from the fluoroscoped image.

BACKGROUND ART

In X-ray fluoroscopic systems including an X-ray fluoroscopic system for industrial use, X-ray camera (two-dimensional X-ray detector) is disposed so as to face an X-ray source, and an X-ray fluoroscoped image of an object of fluoroscopy such as a sample placed between them is displayed or captured.

In X-ray fluoroscopic systems including an X-ray fluoroscopic system for industrial use, a combination of an image intensifier and a CCD camera or a two-dimensional X-ray detector that is made up of an FPD (flat panel detector) (in this specification, they are generally referred to as an X-ray camera) is disposed so as to face the X-ray source, and an X-ray fluoroscoped image of the object of fluoroscopy such as a sample placed between them is captured by the X-ray camera.

In this type of X-ray fluoroscopic system, an XY table for positioning the object of fluoroscopy is usually disposed between the X-ray source and the X-ray camera such that an arbitrary observed point (viewpoint) on the object of fluoroscopy comes within the field of view of the X-ray camera.

Further, some of this type of X-ray fluoroscopic systems is equipped with a tilting mechanism that tilts the X-ray camera to the optical axis center of the X-ray source, and furthermore, a system equipped with a rotating mechanism that relatively rotates the X-ray camera and the XY table around an axis orthogonal to the XY table is also practically used.

Meanwhile, in the X-ray fluoroscopic system equipped with the tilting mechanism, in the state where a desired observed point of the object of fluoroscopy is within the field of view of the X-ray camera by driving the XY table, when the X-ray camera is tilted by the tilting mechanism to allow the observed point to be fluoroscoped from different angles, the observed point comes off from the field of view of the X-ray camera, and it becomes necessary to manually operate the XY table to track the point. Particularly, in the case of performing work at high magnifying power, it is extremely difficult to manually operate the XY table to track the observed point. Further, in the X-ray fluoroscopic system equipped with the rotating mechanism as well, there are cases where the observed point comes off from the field of view of the X-ray camera while moving in an arc shape due to rotation, and it is difficult to track the point while manually operating the XY table.

DISCLOSURE OF THE INVENTION

Problems to be Solved by the Invention

As a technology to solve such problems, an X-ray fluoroscopic system equipped with tilting tracking means is proposed in which a moving amount of the XY table, which is necessary to maintain the observed point, for example, within the center of field of view of the X-ray camera, is obtained by an arithmetic operation to correspond to each tilt angle at each tilting, and the XY table is automatically moved according to the arithmetic operation result (refer to Patent Document 1).

Patent Document 1: Japanese Patent No. 3613121

Meanwhile, according to the above proposed technology, even when the tilting mechanism is driven, the observed point on the object of fluoroscopy does not move but can be maintained, for example, within the center on a fluoroscopy screen by an X-ray camera. However, to maintain within the center, information regarding the observed point on the object of fluoroscopy and a distance between the X-ray source (focal point) and the observed point is needed. Specifically, as schematically shown in FIG. 3, when an observed point V of an object of fluoroscopy W is positioned at the center of the field of view of the X-ray camera I in the state where, for example, a tilt angle of the X-ray camera I is 0, if an X-ray camera I is tilted by θ, it is necessary to move an XY table T in an x-direction by the following amount shown in Equation (1), in order to maintain the observed point V at the center of field of view, assuming that a z-direction distance between the observed point V and an X-ray source (focal point) S be h.

$$a = h * \tan\theta \tag{1}$$

Further, when a position of the observed point V is specified on the screen, to prevent the observed point V of the object of fluoroscopy W from moving in an arc shape when the rotating mechanism is driven, the above-described distance h is necessary in order to reflect the position on the screen and the center of the screen (a point on X-ray optical axis L of the X-ray source S) on a distance between an actual observed point V and the X-ray optical axis L.

Herein, the distance h is a total of a distance z between the X-ray source (focal point) S and the surface of the table T for mounting the object of fluoroscopy W, and a distance d between the surface of the table T and the observed point V, in which the distance z is a known amount but the distance d is generally unknown.

Then, in the above-described proposal, in the case where the distance d between the table surface and the observed point is known, the numerical value of the distance is inputted. In the case where the distance is unknown, the distance h between the X-ray source S and the observed point V is calculated by calibration shown below, and a tracking action is performed by using the calculation result. Specifically, after the observed point is positioned at the center of field of view of the X-ray camera in the state of the tilt angle 0, and such positioning is inputted, the X-ray camera is tilted by an arbitrary angle, the XY table T is manually moved such that the observed point V positions at the center of field of view of the X-ray camera I again in the tilted state, and such movement is inputted. With such a manual operation by the operator, the system calculates the distance h between the observed point V of the object of fluoroscopy W and the X-ray source I, and after that, by an arithmetic operation using the distance h and tilt angle θ of the X-ray camera I at each tilting, automatically drives the XY table T such that the observed point V is tracked to be constantly maintained at the center of field of view of the X-ray camera I.

However, there is a problem that the necessity for the operator to perform the input operation of distance or operation for calibration described above prevents smooth observation work.

The present invention has been created in view of such circumstances, and it is an object of the invention to provide an X-ray fluoroscopic system capable of accurately performing a tracking action during tilting or rotation, without inputting a distance created by a table and an observed point of an object of fluoroscopy (height of observed point) and without performing the above-described operation for calibration.

Means for Solving the Problem

To solve the above-described problem, the X-ray fluoroscopic system of the invention according to Claim 1 comprises: an X-ray source; an X-ray camera disposed at a position to which X-ray from the X-ray source is made incident; an XY table that is provided between the X-ray source and the X-ray camera and used for positioning an object of fluoroscopy mounted thereon; and a tilting mechanism that relatively tilts the X-ray camera to the XY table, wherein the system further comprises: tilting tracking means for calculating a moving amount of the XY table necessary in maintaining the state where an observed point of the object of fluoroscopy is positioned within the field of view of the X-ray camera, in order to automatically move the XY table for tracking the observed point, by an arithmetic operation that uses each tilt angle at each time when the X-ray camera is relatively tilted to the XY table, and a distance h between the X-ray source and the observed point; and update means of data for tracking which uses a defined value or an arbitrary input value as an initial value of the distance h between the X-ray source and the object of fluoroscopy, which is used in the arithmetic operation by the tilting tracking means, and updates the distance h used by the tilting tracking means, by using a shift amount of the observed point which is obtained by specifying the observed point on an image after tracking Herein, in the invention according to Claim 1, relatively tilting the X-ray camera to the XY table may be any one of a constitution in which the X-ray camera is tilted within an irradiating range of X-ray from the X-ray source, a constitution in which the XY table is tilted between the X-ray source and the X-ray camera, and a constitution in which a pair of the X-ray source and the X-ray camera disposed with the XY table laid in-between is tilted.

Further, the X-ray fluoroscopic system of the invention according to Claim 2 comprises: an X-ray source; an X-ray camera disposed at a position to which X-ray from the X-ray source is made incident; an XY table that is provided between the X-ray source and the X-ray camera and used for positioning an object of fluoroscopy mounted thereon; and a rotating mechanism that relatively rotates the X-ray camera and the XY table around an axis orthogonal to the XY table, wherein the system further comprises: rotational tracking means for calculating a moving amount of the XY table necessary in maintaining the state where an observed point of the object of fluoroscopy is positioned within the field of view of the X-ray camera, in order to automatically move the XY table for tracking the observed point, by an arithmetic operation that uses each rotational angle at each time when the X-ray source and the XY table are relatively rotated, and a distance h between the X-ray source and the observed point; and update means of data for tracking which uses a defined value or an arbitrary input value as an initial value of the distance h between the X-ray source and the object of fluoroscopy, which is used in the arithmetic operation by the rotational tracking means, and updates the distance h used by the rotational tracking means, by using a shift amount of the observed point which is obtained by specifying the observed point on an image after tracking.

Further, in the invention according to Claim 2, relatively rotating the X-ray camera and the XY table around an axis orthogonal to the XY table may be either one of a constitution in which an X-ray camera side is rotated around an axis orthogonal to a mounting surface of the object of fluoroscopy of the XY table (vertical axis, for example) with respect to the XY table, a constitution in which the entire XY table is rotated around the axis without rotating the X-ray camera side, and furthermore, a constitution in which the rotation table mounted on the XY table is rotated without rotating the X-ray camera in the same manner.

The present invention attempts to solve the problems by gradually improving the accuracy of the distance h between the X-ray source and the observed point of the object of fluoroscopy by a simple operation during an observing action.

Specifically, in the case where the distance h between the X-ray source and the observed point is necessary in calculating a moving amount of the XY table in a tilting tracking action or a rotational tracking action, a defined value (a substantially default value) or an arbitrary input value (a substantially approximate value) is used as an initial value of the distance. Then, by specifying the observed point on an image obtained by the tracking action, a shift amount of the observed point before/after tracking can be detected, the distance h used for the tracking action, and an error of the distance h with respect to an actual distance can be calculated by using the shift amount, and it becomes possible to perform highly accurate automatic tracking with a simple operation during an observing action by updating the distance h used for the tracking action based on the calculation result.

EXPLANATION OF REFERENCE NUMERALS

Figure 1:
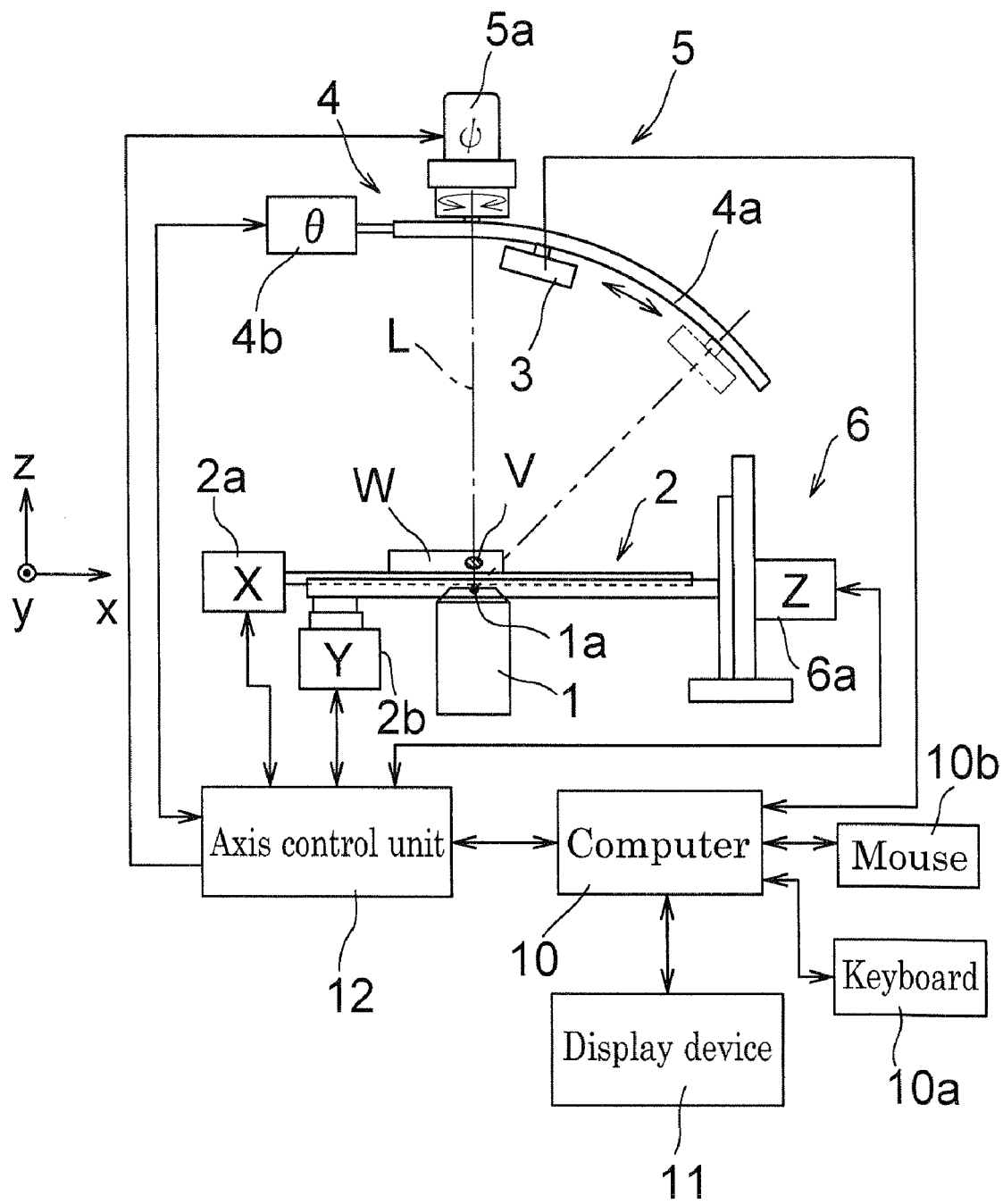
FIG. 1 is a constitution view of an embodiment of the present invention, which is a view showing a schematic view that represents a mechanical constitution, along with a block diagram that represents a system constitution.

1: X-ray source
1a: Focal point
2: XY table
2a: x-axis motor
2b: y-axis motor
3: X-ray camera
4: Tilting mechanism
4a: θ-axis motor
5: Rotating mechanism
5a: φ-axis motor
6: z-axis moving mechanism
6a: z-axis motor 10: Computer
10a: Keyboard
10b: Mouse
11: Display device
12: Control unit
100: Support arm
101: Column
W: Object of fluoroscopy
V: Observed point

BEST MODE FOR CARRYING OUT THE INVENTION

Description will be made below for an embodiment of the present invention referring to the drawings.

FIG. 1 is a constitution view of the embodiment of the present invention, which is a view showing a schematic view that represents a mechanical constitution, along with a block diagram that represents a system constitution.

An X-ray source 1 is disposed such that an optical axis L of X-ray is directed vertically upward, and an XY table 2 along a horizontal plane is provided above the source. An X-ray camera 3 is provided further above the XY table 2 at a required distance. The X-ray is irradiated on an object of fluoroscopy W from below in the state where the object is mounted on the XY table 2, and the X-ray having passed through the object of fluoroscopy W is made incident to the X-ray camera 3. The X-ray camera 3 is an FPD, for example, and output from the camera at each time is taken into a computer 10. An image processing program, which builds an image by using the output from the X-ray camera 3, is installed in the computer 10, and an X-ray fluoroscoped image of the object of fluoroscopy W, which is built by the program, is displayed on a display device 11.

The X-ray camera 3 can be tilted by a tilting mechanism 4 at an arbitrary angle to the optical axis L of the X-ray source 1. The tilting mechanism 4 is constituted of an arc-shaped guiding section 4a that supports the X-ray camera 3 and has the focal point 1a of the X-ray source 1 as a center, and a θ-axis motor 4b that moves the X-ray camera 3 which is supported by the arc-shaped guiding section 4a, along the arc-shaped guiding section 4a as principal elements. When the X-axis and the Y-axis of the XY table 2 are taken on an x-axis and a y-axis respectively, and a vertical axis orthogonal to the axes is taken on a z-axis, the X-ray camera 3 tilts by an arbitrary angle θ to the X-ray optical axis L on an x-z plane by the drive of the tilting mechanism 4.

The arc-shaped guiding section 4a itself of the tilting mechanism 4 is supported rotatably by a frame or the like around an axis on the same axis as the X-ray optical axis L, the arc-shaped guiding section 4a rotates by the drive of a φ-axis motor 5a at an arbitrary angle φ around the X-ray optical axis L as a center in the state of supporting the X-ray camera 3, and these items constitute a rotating mechanism 5.

The above-described XY table 2 moves in an x-axis direction and a y-axis direction by the drive of an x-axis motor 2a and a y-axis drive motor 2b, and the entire XY table 2 can be moved in the vertical direction, that is, direction toward and away from the X-ray source 1 by the drive of a z-axis motor 6a of a z-axis moving mechanism 6.

The motors (2a, 2b) for driving each axis of the XY table 2, the z-axis motor 6a of the Z-axis moving mechanism 6, the θ-axis motor 4a of the above-described tilting mechanism 4 and the φ-axis motor 5b of the rotation mechanism 5 are operated by drive signals from a control unit 12 under the control of the computer 10.

In the computer 10, a tilting tracking program, which is publicly known in the above-described proposal or the like, that tracks the observed point V during tilting of the X-ray camera 3 by an arithmetic operation based on Equation (1) above, or a rotational tracking program, which is publicly known in the above-described proposal or the like, that positions the observed point V at the center of field of view of the X-ray camera 3 to be stationary without forming an arc during rotation of the X-ray camera 3, or moves momently the XY table 2 to correspond to an arc-shaped track of the observed point V, to prevent the observed point V from moving on an image during the rotation of the X-ray camera 3, are installed. A keyboard 10a to which an operator inputs the height d of the observed point V (a distance formed by the surface of the XY table 2 and the observed point V) and a mouse 10b for specifying the observed point V on a screen as described later are connected to the computer 10.

Figure 2:
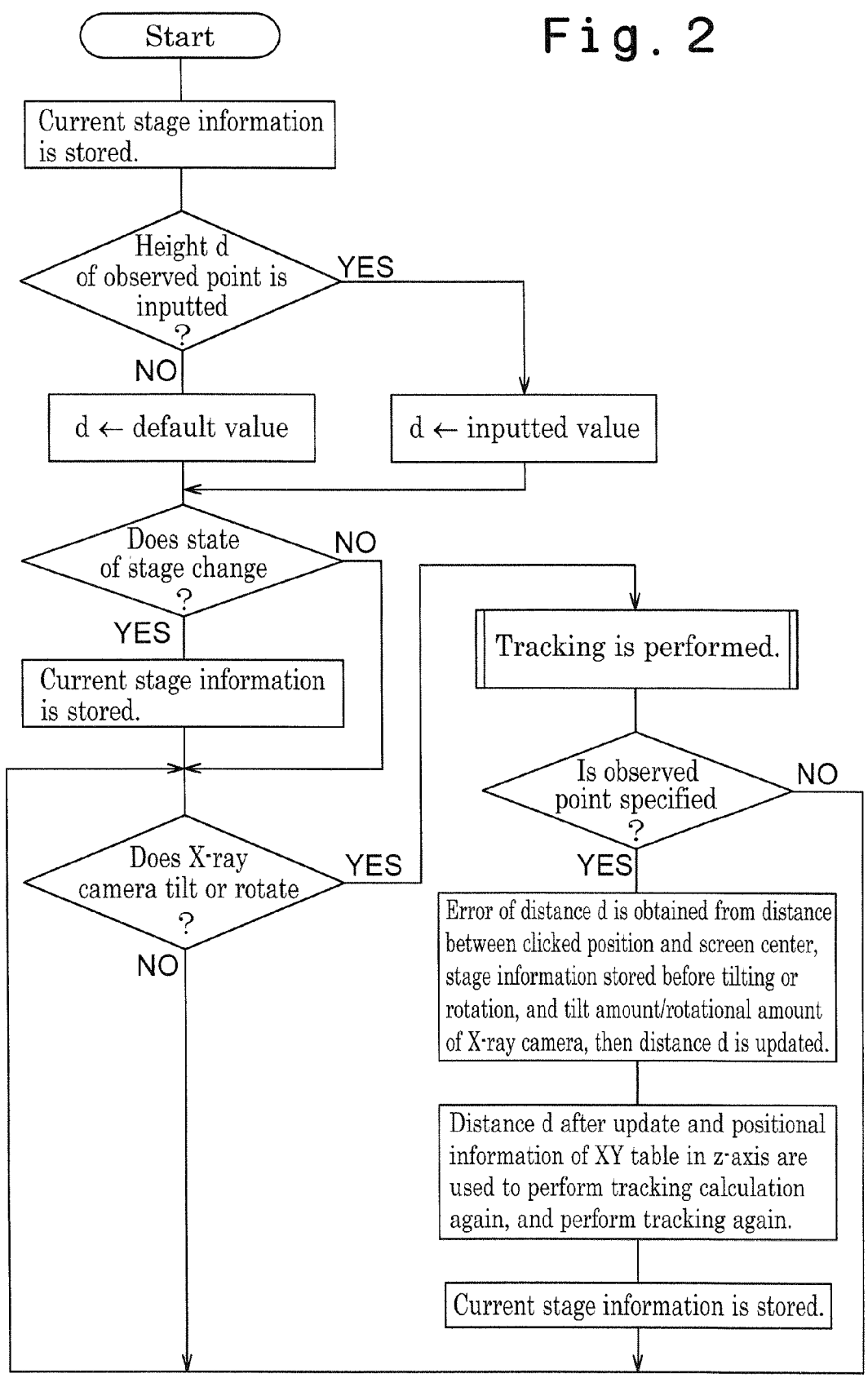
FIG. 2 is a flowchart showing the contents of a program that automatically updates a distance between an observed point and a focal point of an X-ray source for tracking in the embodiment of the present invention.
Figure 3:
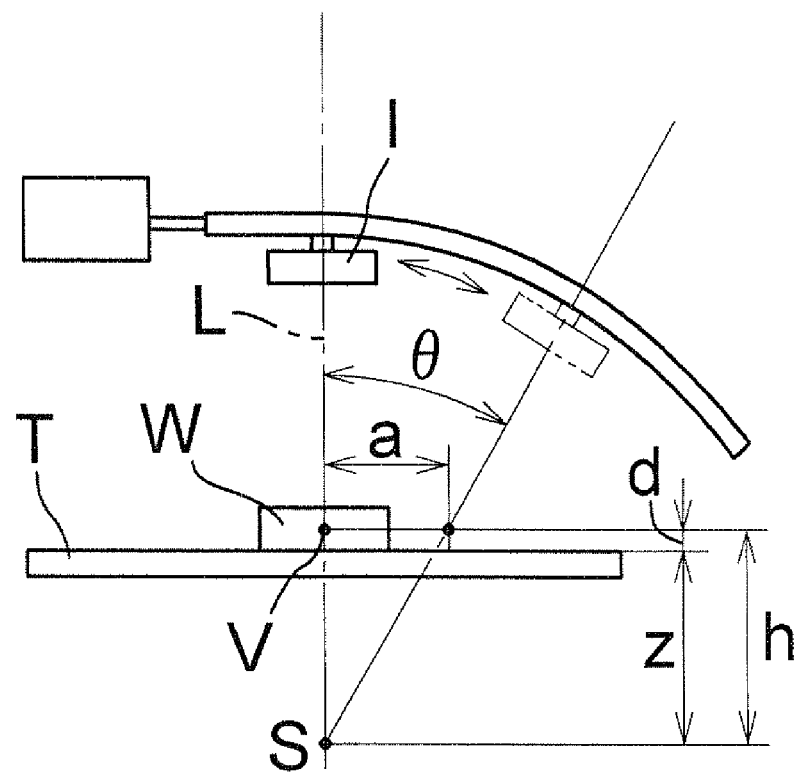
FIG. 3 is an explanatory view of an example of the calculating method of a moving amount of a table for tracking tilt.

Further, a program that automatically updates the distance h between the focal point 1a of the X-ray source 1 and the observed point V on the object of fluoroscopy W, which is necessary in tilting tracking or rotational tracking, by a simple operation in an observation work is written in the computer 10 as shown below. FIG. 2 is a flowchart showing the content of the program.

In the program, a default value (0, for example) is set in advance as the distance d created by the observed point V on the object of fluoroscopy W and the surface of the XY table 2, and the default value is used as an initial value of the distance d when the operator does not input the distance d. Further, when d is inputted, the value is used. Then, at the starting point of the program, and at each time of state change of the stage, that is, movement of the XY table 2 (including the Z-axis moving mechanism 6) and tilting or rotation of the X-ray camera 3 occurs, stage information (positional information of the XY table 2 in x, y, z-axes, tilt angle and rotation angle of the X-ray camera 3) is stored.

Then, in the case where tilting or rotation of the X-ray camera 3 occurs, a tracking action equal to the above-described proposal is performed. In such a case, the distance h between the X-ray source 1 and the observed point V, which is used in calculating a moving amount of the XY table 2, is the sum (h=z+d) of the initial value of the above-described distance d between the observed point V and the surface of the XY table 2 and a distance z between the surface of the XY table 2 and the focal point 1a of the X-ray source 1 at the time of tilting or rotation.

When the observed point V is double-clicked by the mouse 10b on the screen after the tracking, an error of a value of the distance d between the surface of the XY table 2 and the observed point V, that is used at the time of double-click, is obtained from a distance (tracking error) between the clicked position and screen center, stage information stored before tilting or rotation, and a tilt amount/rotational amount of the X-ray camera 3, then the distance d is updated.

Describing a calculation example of the error, in the case where a rotating operation is performed (tilting operation may be or may not be performed) and when coordinate axes are taken as in FIG. 1, a shift amount of the observed point V in a lateral direction of the screen is obtained from the double-clicked position on the screen, and the amount is converted into a shift amount Δx on the X-ray camera 3 while display magnification is taken in consideration. Assuming that the variation of rotational angle be Δφ, the height of the XY table 2 (distance created by the focal point 1a of the X-ray source 1 and the surface of the XY table 2) be z, and the current height of the observed point, that is, a distance from the surface of the XY table 2 to the observed point V be d, an error δx of the height of an the observed point d becomes as follows.

[Equation 1]

$$\delta x = \frac{z+d}{SID \cdot \frac{\sin\Delta\varphi}{\Delta x} + \cos\Delta\varphi} \quad (2)$$

A new height d of the observed point becomes as follows.

[Equation 2]

$$d \leftarrow d - \delta x \quad (3)$$

The rotational tracking action is re-executed by using the height d of the observed point after the update and the stage information before rotation. Thus, the observed point V is brought at the center of the screen. Further, the distance d after update is also used in performing the next tilting or rotational tracking.

In the case where only the tilting operation is performed without the rotating operation, a shift amount of the observed point V in a vertical direction on the screen is obtained from the double-clicked position on the screen, and the amount is converted into a shift amount Δy on the X-ray camera 3 while the display magnification is taken in consideration in the same manner. Assuming that the variation of tilt angle be Δθ, the height of the XY table 2 be z, and the current height of the observed point be d, an error δy of the height d of the observed point becomes as follows.

[Equation 3]

$$\delta y = \frac{z+d}{SID \cdot \frac{\sin\Delta\theta}{\Delta y} + \cos\Delta\theta} \quad (4)$$

A new height d of the observed point thus becomes as follows.

[Equation 4]

$$d \leftarrow d - \delta y \quad (5)$$

The tilting tracking action is re-executed by using the height d of the observed point after the update and the stage information before rotation. Further, similar to the above-described case, the distance d after update is also used in performing the next tilting or rotational tracking.

As described above, even if the height d of the observed point is not inputted at all, a calibration operation for obtaining the distance d is not performed, or even when d is inputted and the value is different from an actual value, the value of d is automatically updated to a more accurate value by specifying the position of the observed point V by double-clicking or the like on the screen after tracking, and performing highly accurate automatic tracking is made possible.

Meanwhile, in the embodiment above, description is made for the X-ray fluoroscopic system of a type in which the X-ray camera 3 is rotated by a rotating operation, but it goes without saying that the present invention can be equally applied to a system having a structure in which the object of fluoroscopy W side is rotated, that is, a system having a structure equipped with a rotation table on or under the XY table 2.

Further, during tilting the X-ray camera 3, a distance SID between the X-ray focal point 1a and the X-ray camera 3 is invariant whereas the fluoroscopy magnification changes due to changes of a distance SOD between the X-ray focal point 1a and the observed point V. However, although a function of automatically changing a z-direction position of the XY table 2 in response to tilt angle in order to maintain the magnification at a constant level is publicly known in the above-described proposal or the like, the above-described distance d is necessary in an action for maintaining the magnification, and it goes without saying that an arithmetic operation for maintaining the fluoroscopy magnification during updating the distance d can be performed by using a new distance d.

Herein, the present invention is not limited to the embodiment with regard to the X-ray source and the table for mounting the object of fluoroscopy thereon, arrangement of the X-ray camera, and a mechanism for performing oblique fluoroscopy, but can be applied to various types of systems. In the following, description will be made for several modified examples. Further, calculation for updating the height of the observed point, which is described above, is applied to the X-ray fluoroscopic system having the structure of the embodiment of FIG. 1. If the structure changes, a calculating formula corresponding to the structure should only be used based on the same concept, and description will be also made for the calculating formula.

Figure 4:
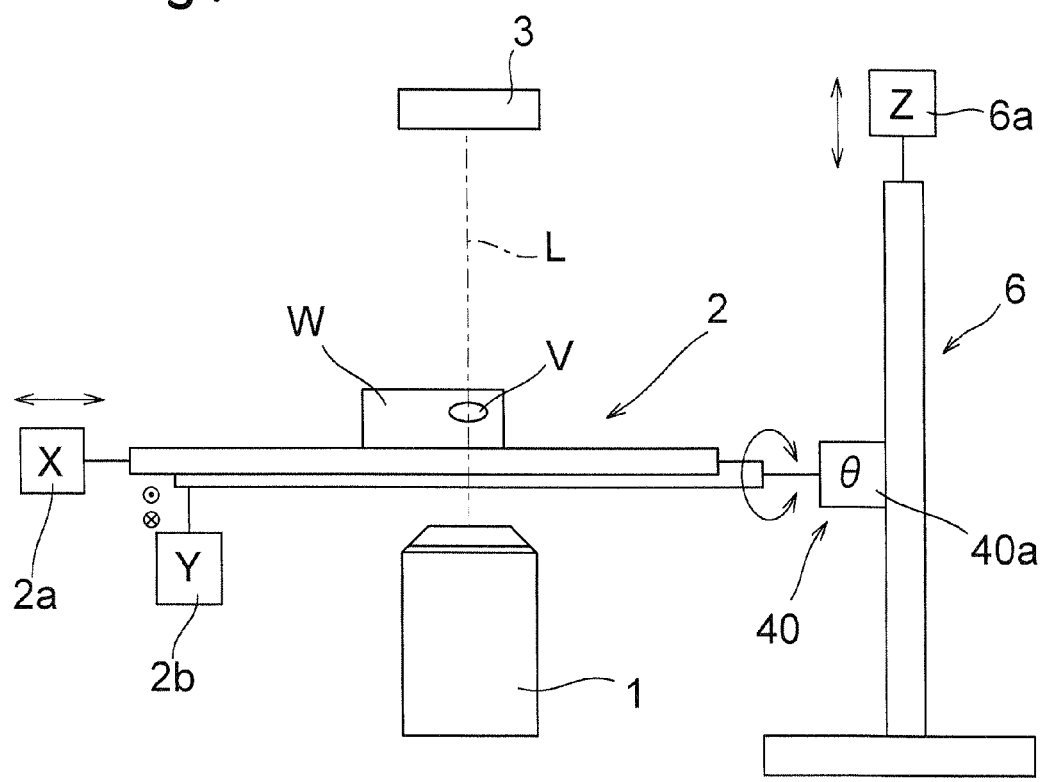
FIG. 4 is a schematic view that represents a mechanical constitution of another embodiment of the present invention.

The example whose schematic view is shown in FIG. 4 is the system of a type in which the X-ray source 1 and the X-ray camera 3 do not move in a state they are disposed to face each other, and the XY table 2 provided between them tilts. Specifically, the X-ray camera 3 does not move in the state where the center of the X-ray camera 3 is positioned on the X-ray optical axis L of the X-ray source 1, the XY table 2 moves in an x-axis direction and a y-axis direction by the x-axis motor 2a and the y-axis motor 2b, and the XY table 2 is supported by the Z-axis moving mechanism 6 similarly to the previous example, and moves in a z-axis direction by the drive of the z-axis motor 6a. Then, in this example, the XY table 2 is designed to be tilted by a tilting mechanism 40 having a θ-axis motor 40a supported by the Z-axis moving mechanism 6 as a drive source, and oblique fluoroscopy can be performed to the observed point V of the object of fluoroscopy W.

Figure 5:
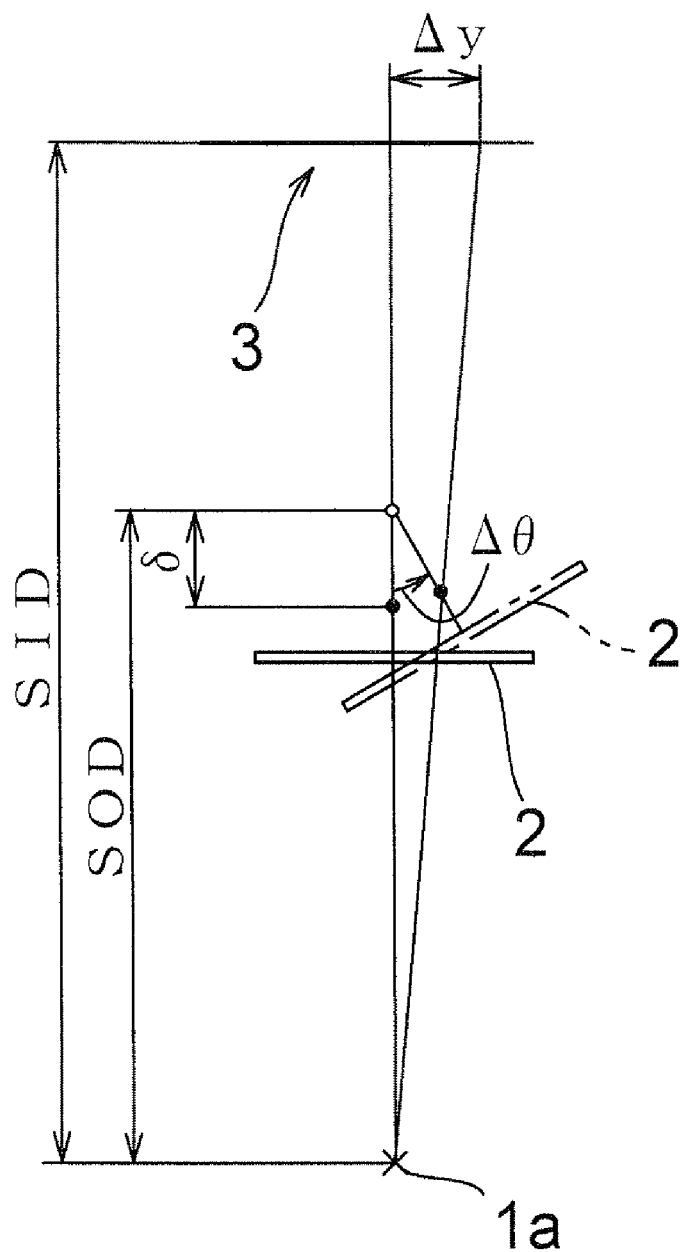
FIG. 5 is a geometrical schematic view for explaining an error calculating formula of the height of the observed point during tilting of the embodiment in FIG. 4.

In the example of FIG. 4, description will be made below for the calculating method of an error amount δ of the height of the observed point when the XY table 2 is tilted while referring to geometrical schematic view (front view) of FIG. 5.

Assuming that the variation of a tilt angle of the XY table 2 be Δθ as shown in the drawing, a distance created by the observed point V and the X-ray focal point 1a used at that time be SOD (corresponds to h in the example above), a distance from the X-ray focal point 1a to the detection plane of the X-ray camera 3 be SID, a true distance from the surface of the XY table 2 to the observed point V be d (true height of observed point), and a shift amount of the observed point V on the detection plane of the X-ray camera 3 before/after tilting Δθ be Δy, the error δ of the height d of the observed point can be obtained by Equation (6) below.

[Equation 5]

$$\delta = \frac{SOD}{\frac{SID}{\Delta y} \cdot \sin\Delta\theta + \cos\Delta\theta} \quad (6)$$

Figure 6:
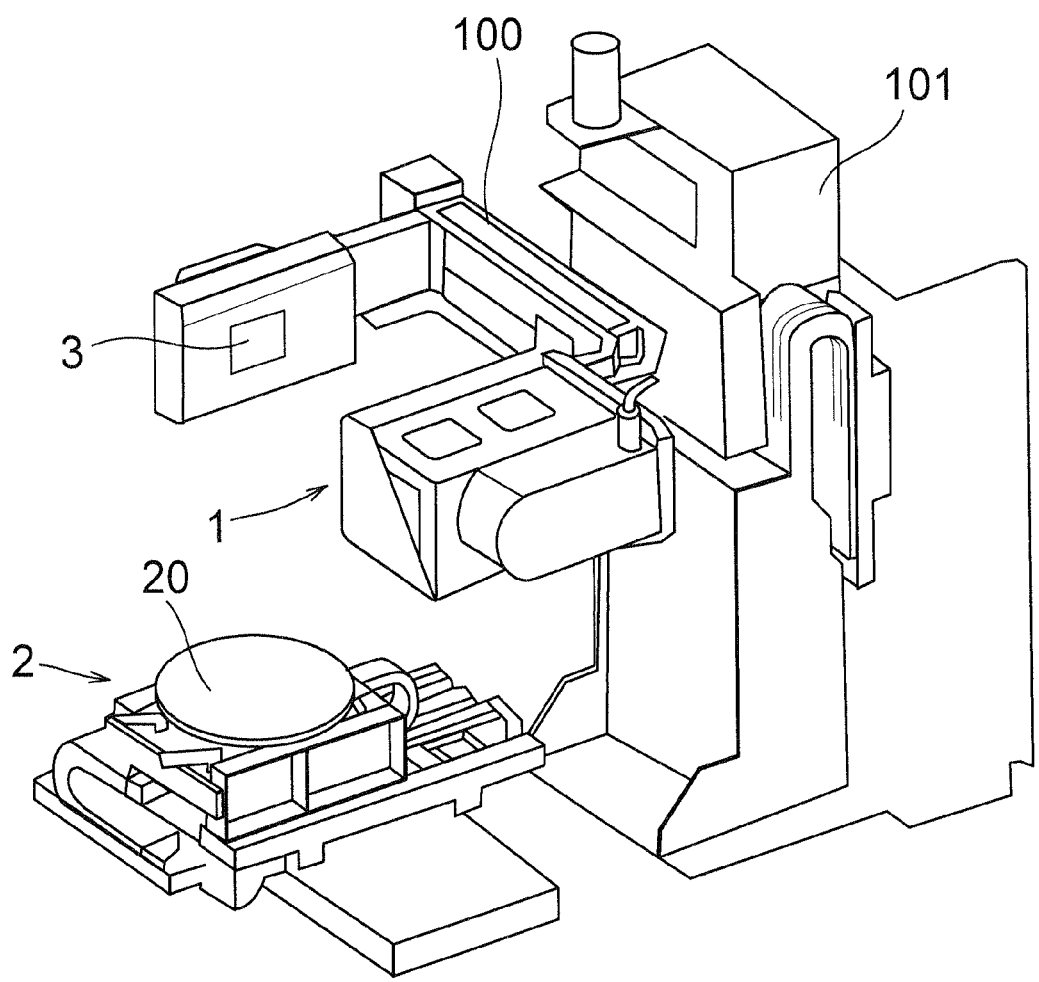
FIG. 6 is a schematic view that represents a mechanical constitution of a still another embodiment of the present invention.

Next, description will be made for an example whose external view is shown in FIG. 6. This example is the system of a type in which the X-ray source 1 and the X-ray camera 3 are supported by a common support arm 100 in the facing state to each other, a pair of the X-ray source 1 and the X-ray camera 3 is tilted to the object of fluoroscopy by tilting the support arm 100 to a column 101 while a horizontal axis is used as a center, and thus realizing oblique fluoroscopy.

In this example, the support arm 100 moves in the z-axis direction with respect to the column 101, a rotation table 20 is disposed on the XY table 2 that moves in x and y-axis directions, and the object of fluoroscopy is disposed on this rotation table 20.

Figure 7:
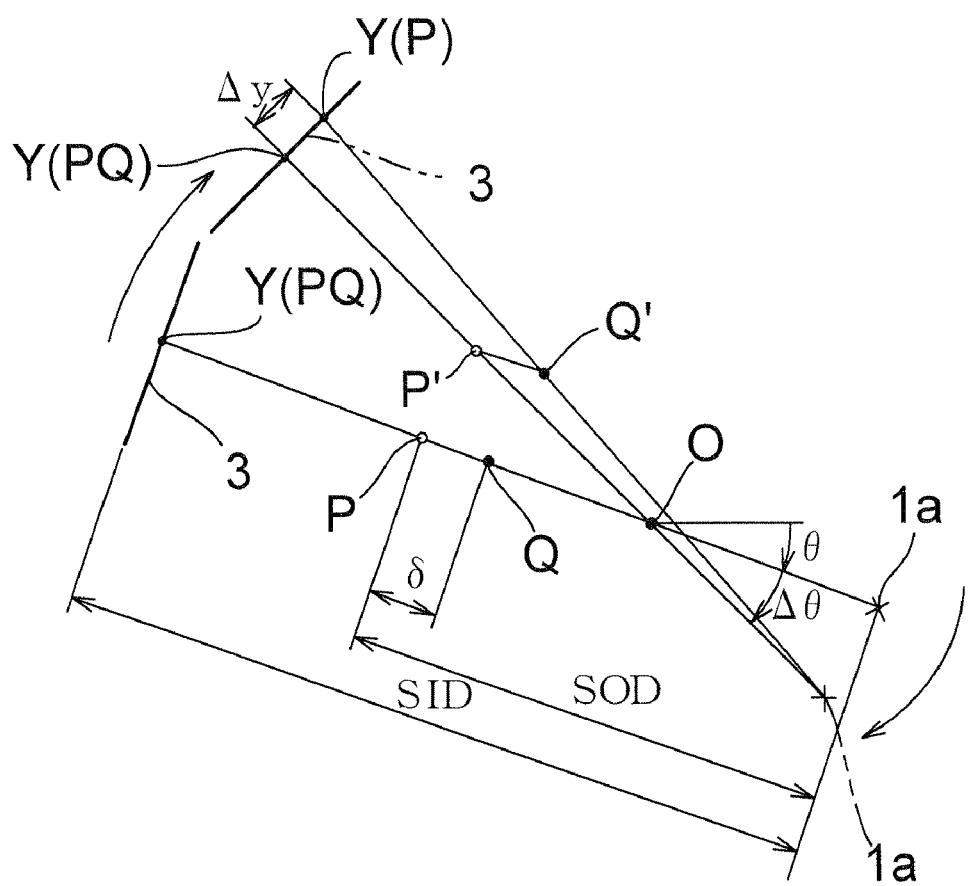
FIG. 7 is a geometrical schematic view for explaining an error calculating formula of the height of the observed point during tilting of the embodiment in FIG. 6.

In the example of FIG. 6, description will be made below for the calculating method of the error amount δ of the height of the observed point when the support arm 100 is tilted while referring to the geometrical schematic view of FIG. 7 (top view).

The tilting center of the support arm 100 is set to O, a tilt angle θ is taken as shown in the drawing, and the variation of the tilt angle is set to Δθ. Further, the position of the observed point V that is set at the time before changing the tilt angle is expressed in P, the true position of the observed point V is expressed in Q, and a projection position of the observed point V to the X-ray camera 3 is expressed in Y (PQ). The error δ of the height of the observed point is shown as shown in the drawing. After changing the tilt angle, a set position of the observed point V becomes P', and the true position of the observed point V is expressed in Q'. The projection position of the observed point V after changing the tilt angle becomes Y (Q), and the position shifts only by Δy with respect to the projection position Y (PQ) before changing the tilt angle. Similarly to the above-described case, assuming that a distance between the set position P of the observed point V, which is used at that time, and an X-ray focal point 21a be SOD, and the distance from the X-ray focal point 1a to the detection plane of the X-ray camera 3 be SID, the error δ of the height of the observed point can be obtained by Equation (7) below.

[Equation 6]

$$\delta = \frac{SOD}{\frac{SID}{\Delta y} \cdot \sin\Delta\theta + \cos\Delta\theta} \quad (7)$$

Next, description will be made for calculation method of the error δ of the height of the observed point when rotation table 20 is rotated in the system shown in FIG. 6, while referring to the geometrical schematic view (top view) of FIG. 8.

Figure 8:
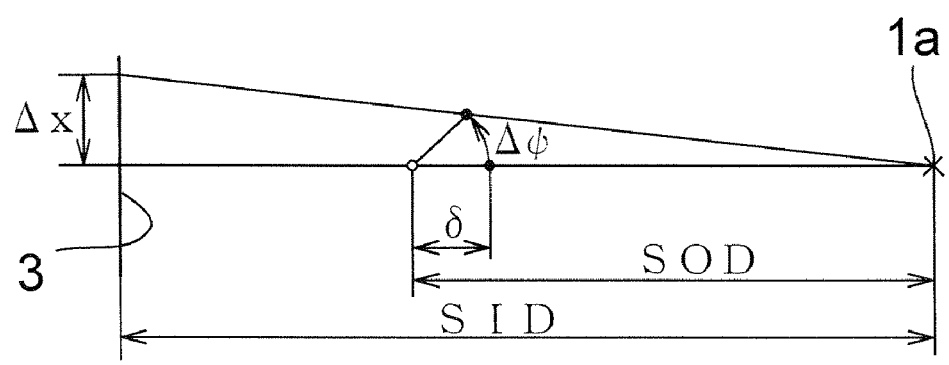
FIG. 8 is a geometrical schematic view for explaining an error calculating formula of the height of the observed point during rotating of the embodiment in FIG. 6.

In FIG. 8, at the time before rotating the rotation table 20, the set position of the observed point V should be P, the true position of the observed point V should be Q, and the true position of the observed point V after rotating the rotation table 20 only by Δφ is expressed in Q'. Further, a distance between the set position of the observed point V and the X-ray focal point 1a should be SOD, and a distance between the X-ray focal point 1a and the detection plane of the X-ray camera 3 should be SID. When the rotation table 20 is rotated only by Δφ, the error δ of the observed point can be obtained by Equation (8) below, assuming that the shift amount of the observed point V on the detection plane of the X-ray camera 3 be Δx.

[Equation 7]

$$\delta = \frac{SOD}{\frac{SID}{\Delta x} \cdot \sin\Delta\phi + \cos\Delta\phi} \quad (8)$$

INDUSTRIAL APPLICABILITY

For example, in the inspection of existence of a defect or the like that exists inside various industrial products, in the case of fluoroscoping an observed point to be focused on a fluoroscoped image of an object of fluoroscopy from a plurality of directions, by using the X-ray fluoroscopic system of the present invention, there are no special operations to make a tracking function effective, such as accurately inputting a distance between an X-ray source and an observed point of the object of fluoroscopy, which is necessary for tilting tracking or rotational tracking, and performing calibration in advance, as in an X-ray fluoroscopic system having a conventional tracking function. And the above-described distance is gradually made highly accurate by a simple operation during observation, so that it becomes possible to smoothly perform an observation work, and higher efficiency of the observation work can be achieved.

The invention claimed is:

1. An X-ray fluoroscopic system comprising:
   an X-ray source;
   an X-ray camera disposed at a position to which X-ray from said X-ray source is made incident;
   an XY table that is provided between said X-ray source and said X-ray camera and used for positioning an object of fluoroscopy mounted thereon; and
   a tilting mechanism that relatively tilts said X-ray camera to said XY table,
   wherein the system further comprises:
   tilting tracking means for calculating a moving amount of said XY table necessary in maintaining the state where an observed point of said object of fluoroscopy is positioned within the field of view of said X-ray camera, in order to automatically move said XY table for tracking said observed point, by an arithmetic operation that uses each tilt angle at each time when said X-ray camera is relatively tilted to said XY table, and a distance h between said X-ray source and said observed point; and
   update means of data for tracking which uses a defined value or an arbitrary input value as an initial value of said distance h between said X-ray source and said object of fluoroscopy, which is used in said arithmetic operation by said tilting tracking means, and updates said distance h used by said tilting tracking means, by using a shift amount of said observed point which is obtained by specifying said observed point on an image after tracking.

2. An X-ray fluoroscopic system comprising:
   an X-ray source;
   an X-ray camera disposed at a position to which X-ray from said X-ray source is made incident;
   an XY table that is provided between said X-ray source and said X-ray camera and used for positioning an object of fluoroscopy mounted thereon; and
   a rotating mechanism that relatively rotates said X-ray camera and said XY table around an axis orthogonal to said XY table, wherein the system further comprises:

rotational tracking means for calculating a moving amount of said XY table necessary in maintaining the state where an observed point of said object of fluoroscopy is positioned within the field of view of said X-ray camera, in order to automatically move said XY table for tracking said observed point, by an arithmetic operation that uses each rotational angle at each time when said X-ray source and said XY table are relatively rotated, and a distance h between said X-ray source and said observed point; and update means of data for tracking which uses a defined value or an arbitrary input value as an initial value of said distance h between said X-ray source and said object of fluoroscopy, which is used in said arithmetic operation by said rotational tracking means, and updates said distance h used by said rotational tracking means, by using a shift amount of said observed point which is obtained by specifying said observed point on an image after tracking.

* * * * *